United States Patent
Barney et al.

(10) Patent No.: US 8,528,543 B2
(45) Date of Patent: Sep. 10, 2013

(54) SPACER FOR CONNECTING INHALER DEVICE TO MASK

(75) Inventors: Brian Barney, Essex (GB); Rachel Striebig, London (GB); Siobhan D'Gama, London (GB)

(73) Assignee: TEVA Animal Health, Inc., St. Joseph, MO (US)

( * ) Notice: Subject to any disclaimer, the term of this patent is extended or adjusted under 35 U.S.C. 154(b) by 1190 days.

(21) Appl. No.: 12/350,655

(22) Filed: Jan. 8, 2009

(65) Prior Publication Data

US 2009/0223517 A1    Sep. 10, 2009

Related U.S. Application Data

(63) Continuation of application No. 11/945,003, filed on Nov. 26, 2007, now abandoned, which is a continuation of application No. 10/589,913, filed as application No. PCT/US2005/011370 on Apr. 1, 2005, now abandoned.

(30) Foreign Application Priority Data

Apr. 1, 2004  (GB) .................................. 0407472.0

(51) Int. Cl.
*B05B 1/26* (2006.01)
*A61M 11/00* (2006.01)
*A61M 15/00* (2006.01)

(52) U.S. Cl.
USPC ............. 128/200.18; 128/200.14; 128/203.12

(58) Field of Classification Search
USPC .................... 128/200.14, 200.18, 200.23, 128/203.12, 203.15, 203.23, 203.29, 128/203.24, 205.23, 205.24, 205.25, 128/206.21, 206.28, 207.15
See application file for complete search history.

(56) References Cited

U.S. PATENT DOCUMENTS

| | | | | | |
|---|---|---|---|---|---|
| 4,470,412 | A | * | 9/1984 | Nowacki et al. | 128/200.18 |
| 4,809,692 | A | * | 3/1989 | Nowacki et al. | 128/206.24 |
| 5,031,610 | A | * | 7/1991 | Armstrong et al. | 128/200.23 |
| 5,224,472 | A | * | 7/1993 | Pesenti et al. | 128/200.14 |
| D339,416 | S | * | 9/1993 | Maher | D24/110 |
| 5,385,140 | A | * | 1/1995 | Smith | 128/200.23 |
| 5,427,089 | A | * | 6/1995 | Kraemer | 128/200.23 |
| 5,611,332 | A | * | 3/1997 | Bono | 128/200.18 |
| 5,809,996 | A | * | 9/1998 | Alldredge | 128/200.23 |

(Continued)

FOREIGN PATENT DOCUMENTS

| | | |
|---|---|---|
| DE | 38 27 636 A1 | 2/1989 |
| EP | 0 009 667 A1 | 4/1980 |
| GB | 2 000 555 A | 1/1979 |
| WO | WO-01/35856 A1 | 5/2001 |

*Primary Examiner* — Justine Yu
*Assistant Examiner* — Christopher Miller
(74) *Attorney, Agent, or Firm* — RatnerPrestia

(57) ABSTRACT

A spacer for connecting an inhaler device to a mask, including an elongated cylindrical first member extending along a central axis between a proximal end adapted to receive an inhaler device and a distal end having a particle reflecting surface, and wherein the first member has an inner channel extending along the central axis, and an elongated cylindrical second member extending along a central axis between a closed proximal end and a distal end adapted to connect to a mask, wherein the second member defines an inner channel extending along the central axis of the second member and wherein the first member and the second member are connected such that the inner channels of the members are joined lengthwise.

19 Claims, 12 Drawing Sheets

(56) References Cited

U.S. PATENT DOCUMENTS

| | | | |
|---|---|---|---|
| 5,855,202 A * | 1/1999 | Andrade | 128/200.14 |
| 5,988,160 A * | 11/1999 | Foley et al. | 128/200.22 |
| 6,039,042 A * | 3/2000 | Sladek | 128/200.23 |
| 6,138,668 A | 10/2000 | Patton et al. | |
| 6,293,279 B1 * | 9/2001 | Schmidt et al. | 128/200.23 |
| 6,394,085 B1 * | 5/2002 | Hardy et al. | 128/203.15 |
| 6,435,177 B1 * | 8/2002 | Schmidt et al. | 128/200.23 |
| 6,698,422 B2 * | 3/2004 | Fugelsang et al. | 128/200.14 |
| 7,631,643 B2 * | 12/2009 | Morrison et al. | 128/202.22 |
| 7,721,729 B2 * | 5/2010 | Von Hollen et al. | 128/200.14 |
| 8,001,962 B2 * | 8/2011 | Sheiman | 128/200.14 |
| 2004/0000307 A1 | 1/2004 | Khan | |
| 2005/0217667 A1 * | 10/2005 | Dhuper et al. | 128/200.23 |

\* cited by examiner

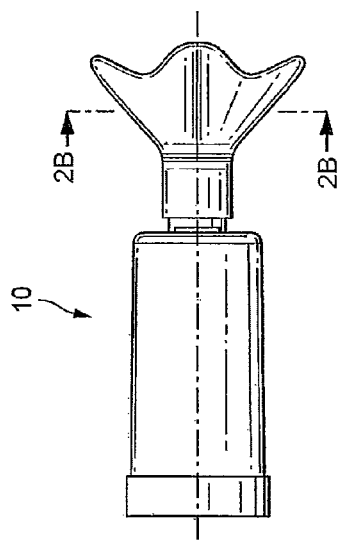
FIG. 2A
FIG. 2B
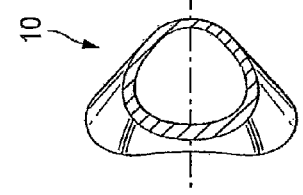
FIG. 1A
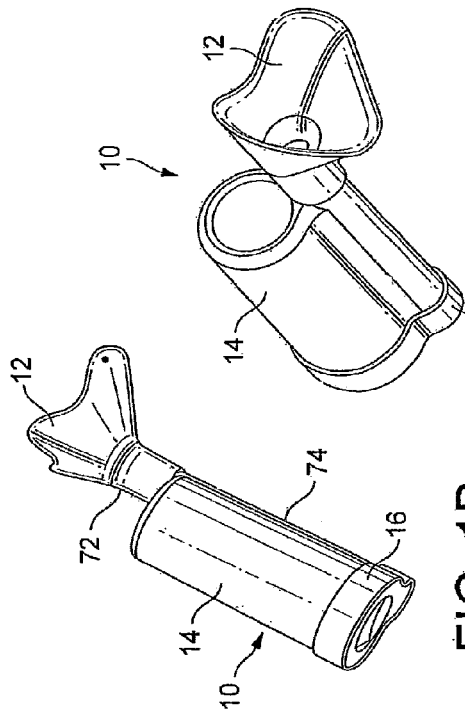
FIG. 1B
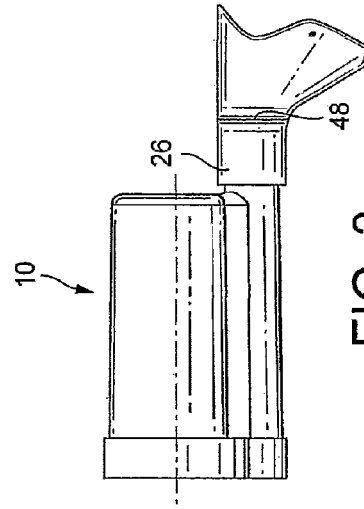
FIG. 3
FIG. 4A
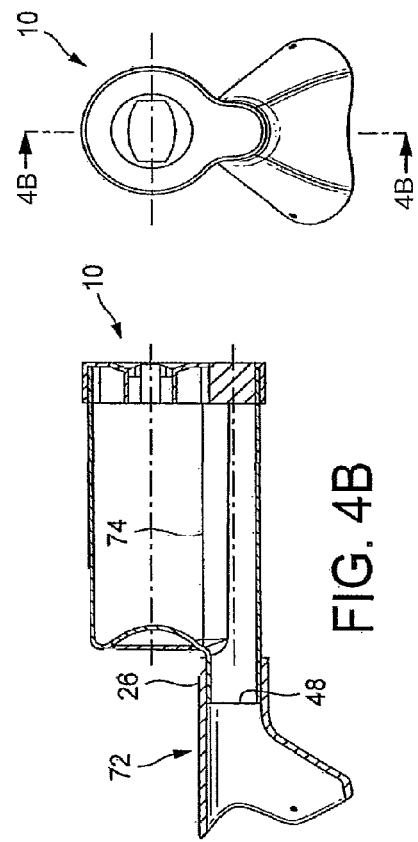
FIG. 4B

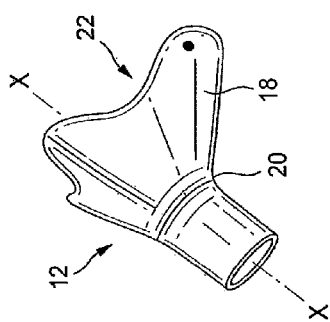
FIG. 5B
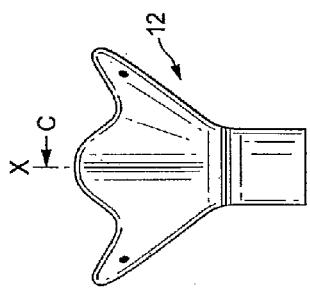
FIG. 6A
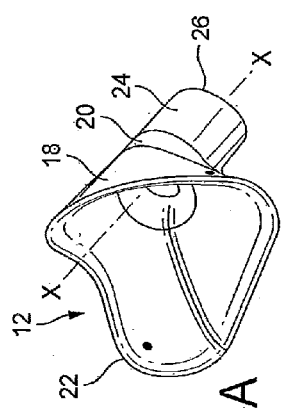
FIG. 5A
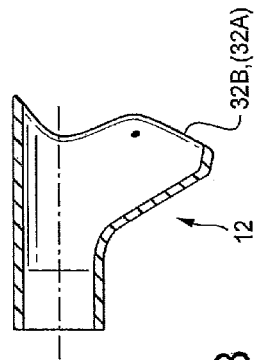
FIG. 9
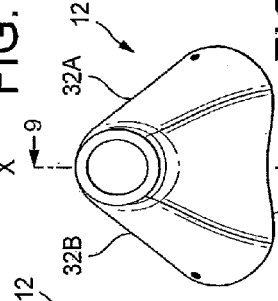
FIG. 7B
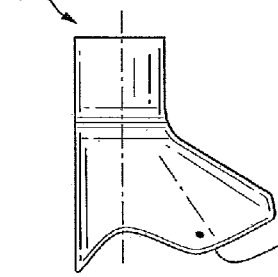
FIG. 8
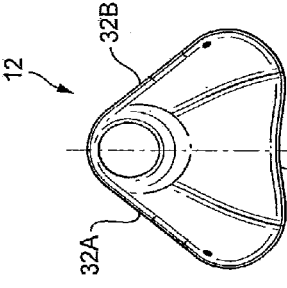
FIG. 7A
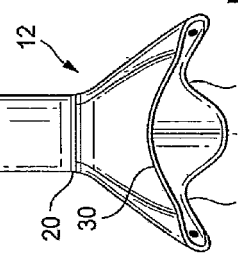
FIG. 6B

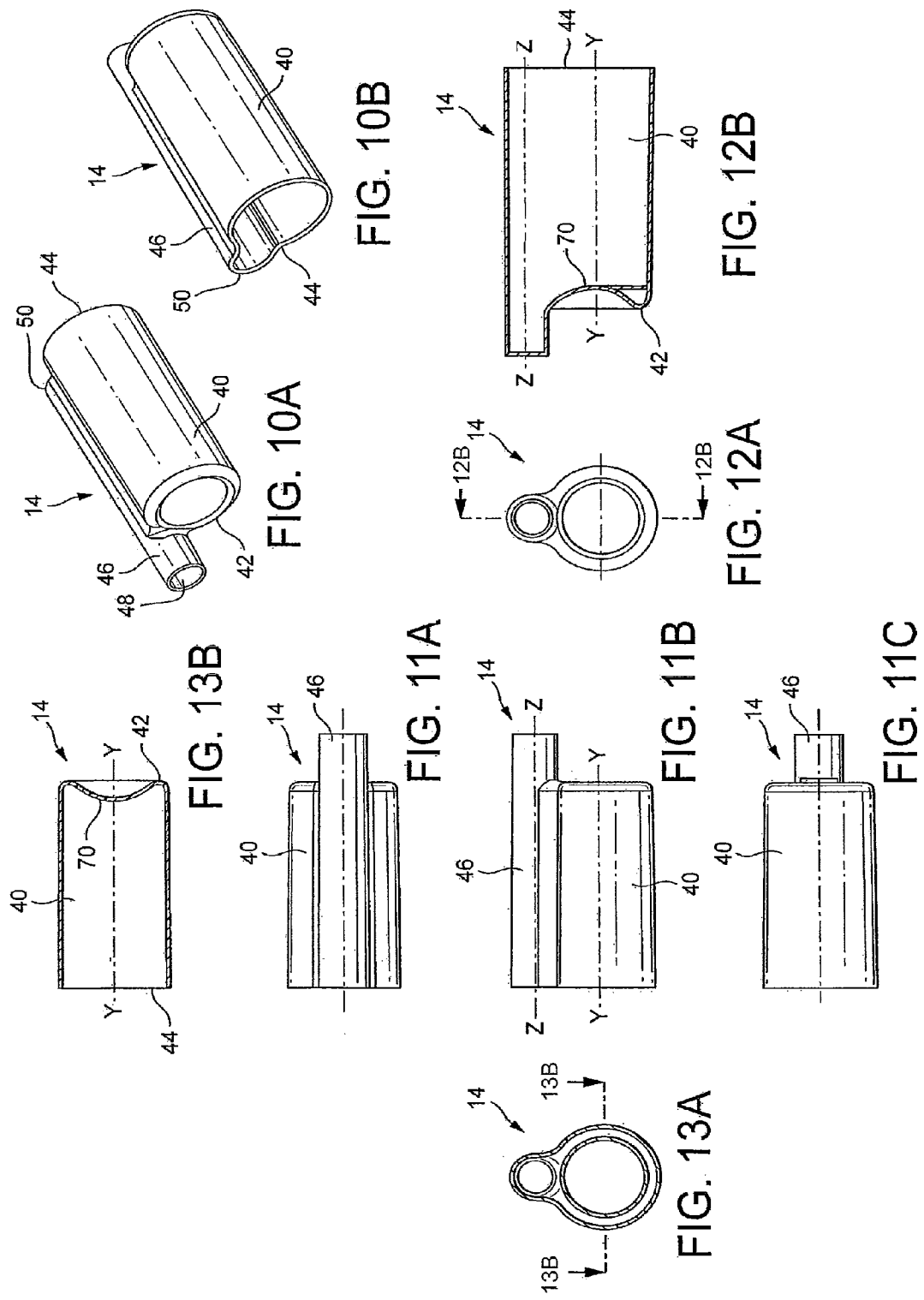

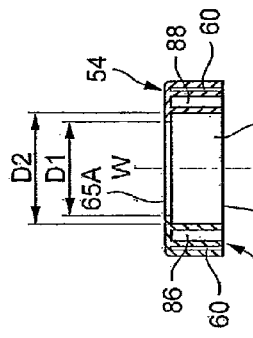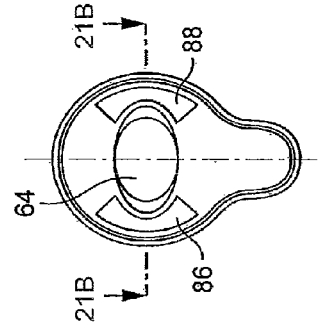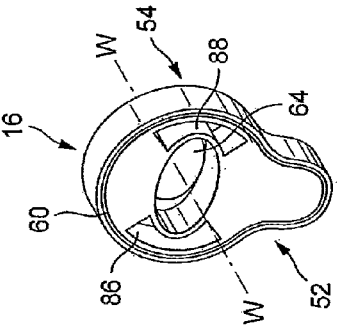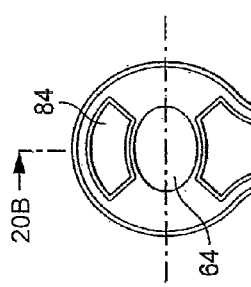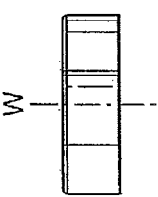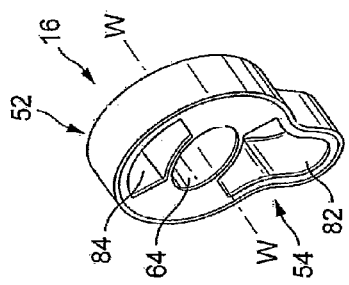

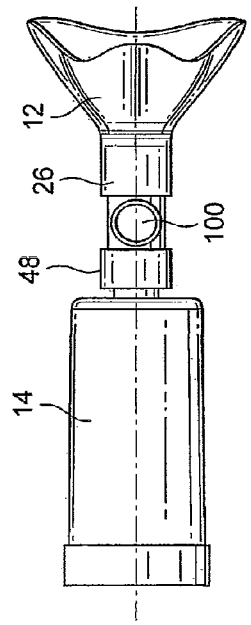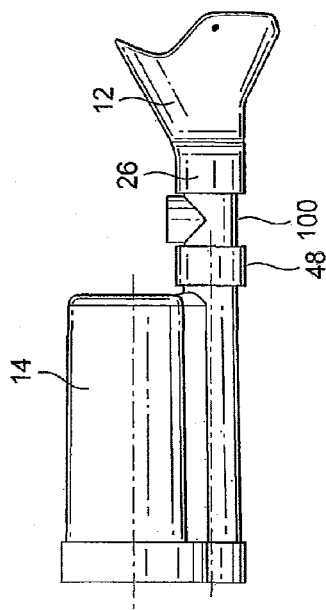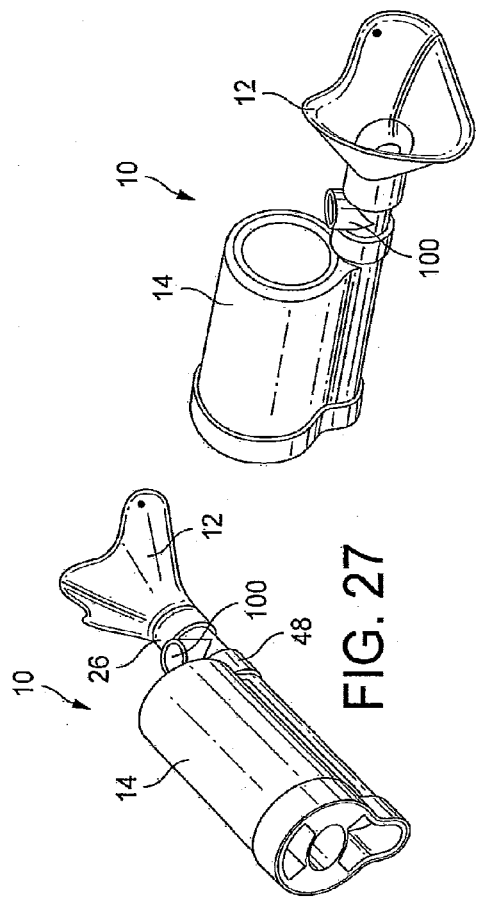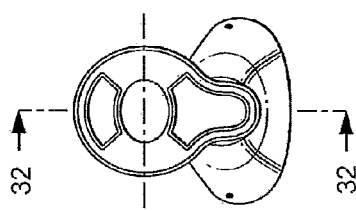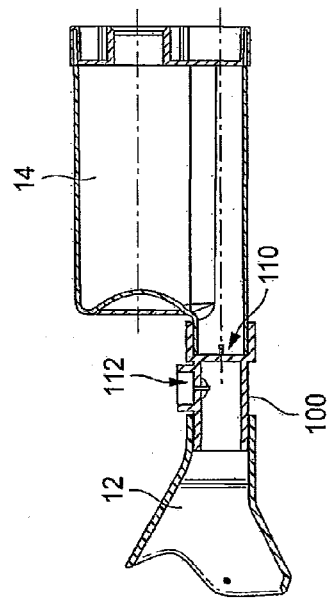

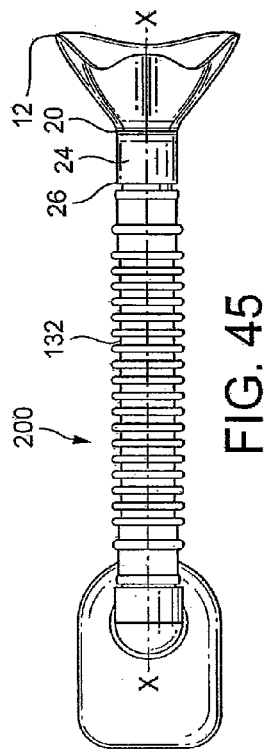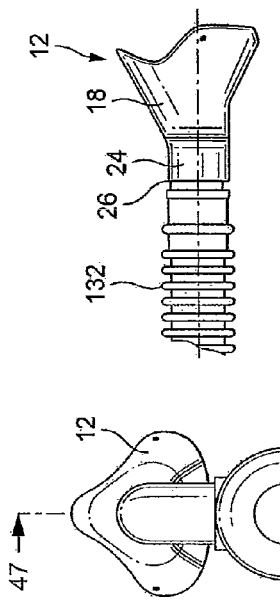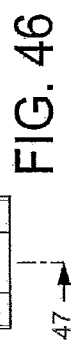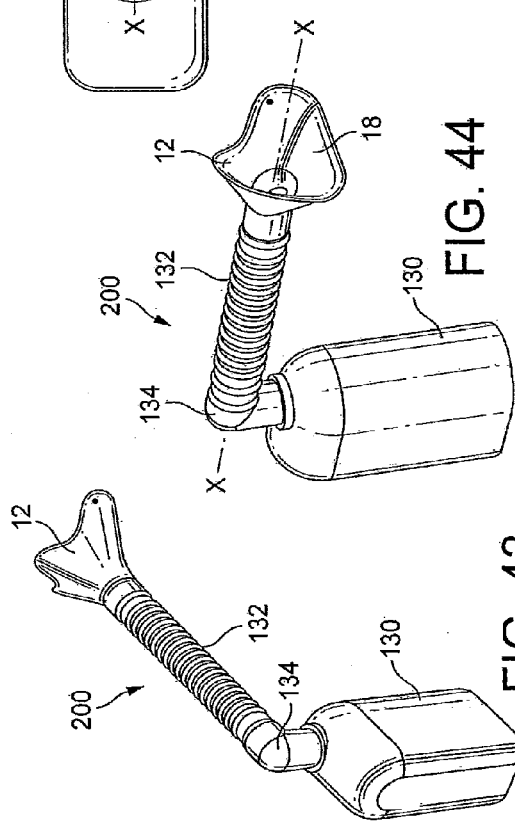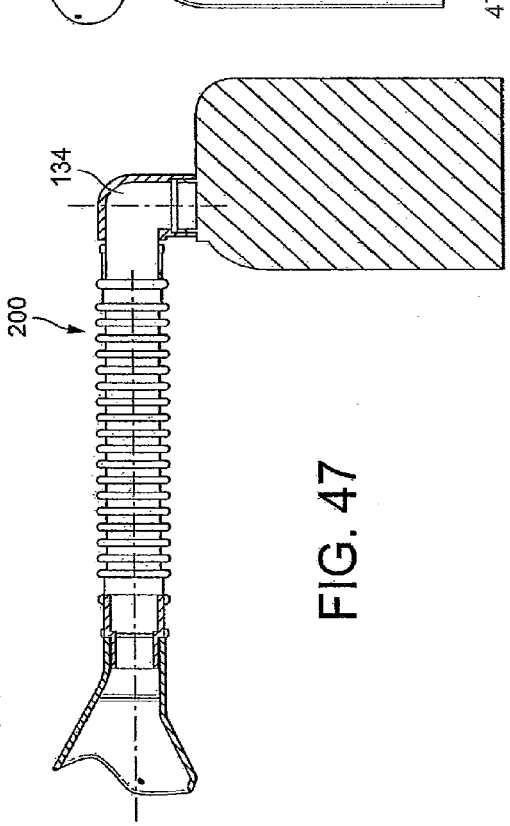
FIG. 45
FIG. 46
FIG. 47
FIG. 48
FIG. 43
FIG. 44

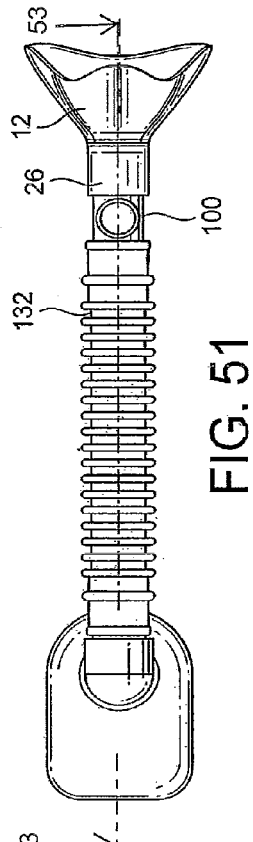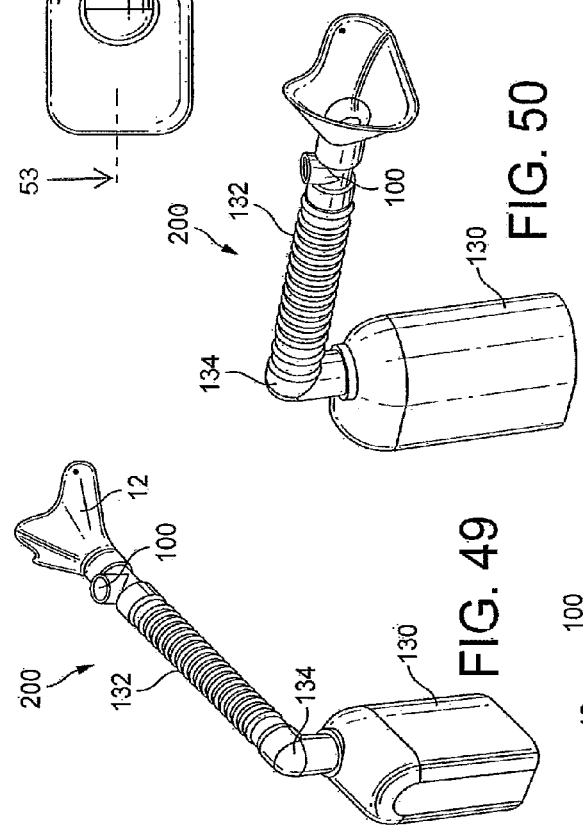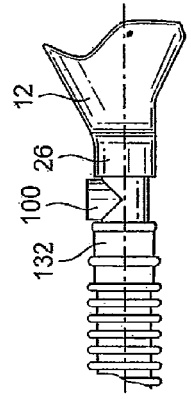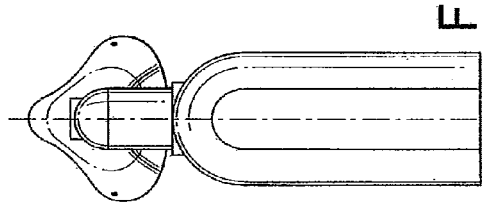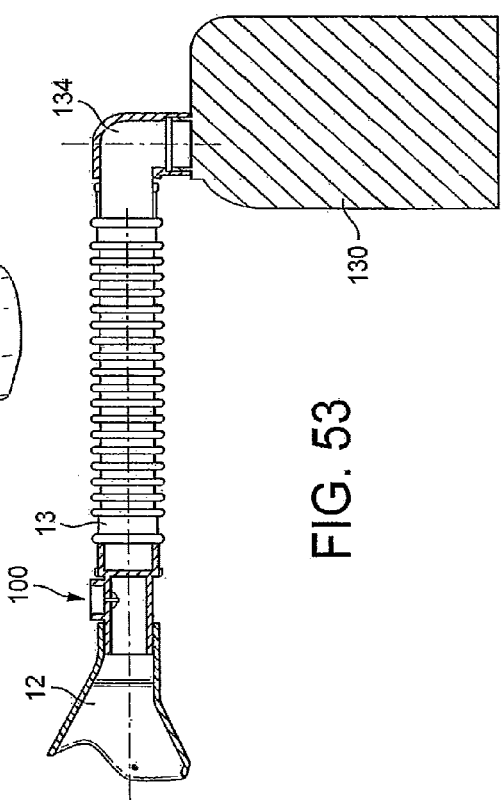

SPACER FOR CONNECTING INHALER DEVICE TO MASK

CROSS-REFERENCE TO RELATED APPLICATIONS

This application is a continuation application of U.S. patent application Ser. No. 11/945,003, filed Nov. 26, 2007, which is continuation application of U.S. patent application Ser. No. 10/589,913, filed Aug. 18, 2006, which is a national phase entry under 35 U.S.C. §371 of International Application No. PCT/US2005/011370, filed Apr. 1, 2005, published in English, which claims the benefit of United Kingdom Patent Application No. 0407472.0, filed Apr. 1, 2004. The disclosure of all of said applications are incorporated by reference herein.

FIELD OF THE DISCLOSURE

The present disclosure relates to the delivery of drugs to animals, and more particularly to devices for enabling the delivery of drugs or medicaments to animals for pulmonary or nasal absorption via the mouth and/or nose.

BACKGROUND OF THE INVENTION

The delivery of a drug or a medicament to an animal, and in particular a mammal, such as a human, a dog or a cat, for pulmonary or nasal absorption is desired in many circumstances. Direct application, such as by a spray or aerosol delivery device, or a dry powder delivery device, is difficult due to movements of the animal. To enable such application of medicaments, in the prior art, an elongated, generally cup-shaped "mask" is often provided, having a relatively large open base end for fitting over an animal's nostrils or muzzle and having a medicament administration port opposite that base end for connecting to a mouthpiece of a medicament dispensing device. Typically, the mask is made out of a semi rigid material (e.g., sheet polycarbonate) and is provided in various sizes for use with different sized animals.

A common problem with prior art mask devices is that prior art mask devices fail to provide a comfortable and tight seal around the animal's mouth and nostrils. Prior art devices also fail to efficiently direct the medicament from the medicament dispensing device to the mask, and then to the animal's mouth or nostrils. Therefore, it is desirable when delivery medicaments to small animals for pulmonary or nasal absorption via the mouth and/or nose that the delivery device can provide a comfortable fit, and a tight and secure seal around the animal's mouth and nostrils. It is also desirable to have a delivery device that can efficiently direct medicament from the medicament dispensing device to the animal's mouth or nostrils for inhalation.

SUMMARY OF THE DISCLOSURE

According to one aspect, the present disclosure provides a spacer for connecting an inhaler device to a mask. The spacer includes an elongated cylindrical first member and an elongated cylindrical second member. The first member extends along a central axis between a proximal end adapted to receive an inhaler device and a distal end having a particle reflecting surface, and wherein the first member has an inner channel extending along the central axis. The second member extends along a central axis between a closed proximal end and a distal end adapted to connect to a mask, wherein the second member defines an inner channel extending along the central axis of the second member. The first member and the second member are connected such that the inner channels of the members are joined lengthwise.

Additional aspects and advantages of the present disclosure will become readily apparent to those skilled in this art from the following detailed description, wherein exemplary embodiments of the present disclosure are shown and described, simply by way of illustration. As will be realized, the present disclosure is capable of other and different embodiments and its several details are capable of modifications in various obvious respects, all without departing from the disclosure. Accordingly, the drawings and description are to be regarded as illustrative in nature, and not as restrictive.

BRIEF DESCRIPTION OF THE DRAWINGS

FIGS. 1A and 1B are perspective end views of an exemplary embodiment of a delivery device constructed in accordance with the present disclosure;

FIG. 2A shows a top plan view of the delivery device of FIGS. 1A and 1B;

FIG. 2B is a sectional view of the device of FIGS. 1A and 1B taken along line A-A in FIG. 2A;

FIG. 3 is a side elevation view of the device of FIGS. 1A and 1B;

FIG. 4A is an end view of the device of FIGS. 1A and 1B;

FIG. 4B is a sectional view of the device of FIGS. 1A and 1B taken along line B-B in FIG. 4A;

FIG. 5A and FIG. 5B are perspective end views of a mask of the device of FIGS. 1A and 1B;

FIG. 6A is a top plan view of the mask of FIG. 5A and FIG. 5B;

FIG. 6B is a bottom plan view of the mask of FIG. 5A and FIG. 5B;

FIG. 7A is a front elevation view of the mask of FIG. 5A and FIG. 5B;

FIG. 7B is a rear elevation view of the mask of FIG. 5A and FIG. 5B;

FIG. 8 is a side elevation view of the mask of FIG. 5A and FIG. 5B;

FIG. 9 is a sectional view of the mask of FIG. 5A and FIG. 5B taken along line 9-9 in FIG. 7B;

FIGS. 10A and 10B are perspective end views of an exemplary embodiment of a spacer of the device of FIGS. 1A and 1B;

FIG. 11A is a top plan view of the spacer of FIGS. 10A and 10B;

FIG. 11B is a side elevation view of the spacer of FIGS. 10A and 10B;

FIG. 11C is a bottom plan view of the spacer of FIGS. 10A and 10B;

FIG. 12A is a front elevation view of the spacer of FIGS. 10A and 10B;

FIG. 12B is a sectional view of the spacer of FIGS. 10A and 10B taken along line 12B-12B in FIG. 12A;

FIG. 13A is a rear elevation view of the spacer of FIGS. 10A and 10B;

FIG. 13B is a sectional view of the spacer of FIGS. 10A and 10B taken along line 13B-13B in FIG. 13A;

FIG. 19A and FIG. 19B are perspective end views of another exemplary embodiment of an end wall adapter for use with the device of FIGS. 1A and 1B, and that attaches to and closes an end of the spacer of FIGS. 10A and 10B;

FIG. 20A is a front elevation view of the spacer adapter 16 of FIGS. 19A and 19B;

FIG. 20B is a sectional view of the spacer adapter of FIGS. 19A and 19B taken along line 20B-20B in FIG. 20A;

FIG. 21A is a rear elevation view of the spacer adapter of FIGS. 19A and 19B;

FIG. 21B is a sectional view of the spacer adapter of FIGS. 19A and 19B taken along line 21B-21B in FIG. 21A;

FIG. 22A is a top plan view of the spacer adapter of FIGS. 19A and 19B;

FIG. 22B is a bottom plan view of the spacer adapter of FIGS. 19A and 19B;

FIG. 23 is a side elevation view of the spacer adapter of FIGS. 19A and 19B;

FIGS. 27 and 28 are perspective end views of a further exemplary embodiment of a delivery device constructed in accordance with the present disclosure and including a T-shape element between the mask and the spacer;

FIG. 29 is a top plan view of the delivery device of FIGS. 27 and 28;

FIG. 30 is a side elevation view of the delivery device of FIGS. 27 and 28;

FIG. 31 is an end elevation view of the delivery device of FIGS. 27 and 28;

FIG. 32 is a sectional view of the delivery device of FIGS. 27 and 28 taken along line 32-32 in FIG. 31;

FIGS. 43 and 44 are perspective end views of an exemplary embodiment of a medicament delivery device constructed in accordance with the present disclosure and including a nebulizer and a mask connected through a hose;

FIG. 45 is a top plan view of the medicament delivery device of FIGS. 43 and 44;

FIG. 46 is a rear elevation view of the medicament delivery device of FIGS. 43 and 44;

FIG. 47 is a sectional view of the medicament delivery device of FIGS. 43 and 44 taken along line 47-47 in FIG. 46;

FIG. 48 is an enlarged side elevation view of the mask and a portion of the hose of the medicament delivery device of FIGS. 43 and 44;

FIGS. 49 and 50 are perspective end views of another exemplary embodiment of a medicament delivery device constructed in accordance with the present disclosure, and which is similar to the device illustrated in FIGS. 43 through 48, but further includes a T-shape element similar to the T-shape element of FIGS. 27 through 42 connecting the hose and the mask;

FIG. 51 is a top plan view of the delivery device of FIG. 49;

FIG. 52 is an end view of the delivery device of FIG. 49;

FIG. 53 is a sectional view of the delivery device of FIG. 49 taken along the line 53-53 in FIG. 51;

FIG. 54 is a fragmentary side elevational view of the delivery device of FIG. 49;

DETAILED DESCRIPTION OF THE INVENTION

Figure 16B:
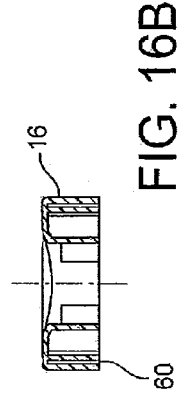
FIG. 16B is a sectional view of the spacer adapter of FIGS. 14A and 14B taken along line 16B-16B in FIG. 16A.

The present disclosure provides a medicament delivery device, which can be used with a medicament dispenser, such as an inhaler or nebulizer, to deliver medicament for inhalation by an animal. Exemplary embodiments of the present disclosure are shown in the attached figures.

FIGS. 1A through 4B show an exemplary embodiment of a delivery device 10 constructed in accordance with the present disclosure. The delivery device 10 includes a mask 12, a spacer 14, and a spacer adaptor 16. The mask 12 is shown in greater detail in FIGS. 5A-9. The mask 12 is intended for use with any mammal, particularly, is intended to but is not limited to use with small mammals. Foremost among such mammals are humans, although the disclosure is not intended to be so limited, and is applicable to veterinary uses, such as with cats. Thus, in accordance with the disclosure, "mammals" or "mammal in need" include humans as well as non-human mammals, particularly domesticated animals including, without limitation, cats and dogs. The word "animal" used in this application also includes humans and nonhuman mammals. The terms "proximal" and "distal" are known terms used to denote relative locations, and as used herein, the terms denote relative locations with the point of reference being the mammal being treated during use.

The mask 12 includes a base portion 18 extending along an axis X and having a relatively small upstream end 20 and a relatively large downstream end 22, and a tubular portion 24 extending along the axis X from the upstream end 20 of the base portion 18 to a distal end 26, which is connected to the spacer 14. The base portion 18 and the tubular portion 24 are preferably integrally constructed. The base portion 18 preferably has a shape similar to a pyramid. A person skilled in the art should appreciate that other equivalent shapes also can be used for the mask 12. For example, the mask 12 can include only the pyramidal shape base portion 18 without the tubular portion 24, and the upstream end 20 is adapted for connecting with the spacer 14. The mask 12 is preferably made from a flexible, light-weight, non-porous material, such as a suitable thermoplastic or rubber.

The downstream end 22 of the mask 12 is adapted for fitting over an animal's face, such that the mask 12 covers the animal's mouth and nostrils, and provides a comfortable and tight seal around the animal's mouth and nostrils. The downstream end 22 preferably includes three edge sections: a bottom edge section 30, and two side edge sections 32A and 32B.

The two side edge sections 32A and 32B join with each other at the top of the downstream end 22, and join with the bottom edge section 30 at two bottom corners. As best shown in the bottom view in FIG. 6B, the bottom edge section 30 is preferably shaped to slightly curve toward the upstream end 20 in a substantially "V" shape, and as best shown in side views in FIGS. 8 and 9, the side edge sections 32A and 32B also are preferably shaped to curve, from the junction with the bottom edge section 30, first toward the upstream end 20 and then, away from the upstream end 20, forming a substantially "S" shape periphery (FIG. 9 shows a substantially "S" shape periphery, and FIG. 8 shows a mirror image of "S" viewed from an opposite side).

The base portion 18 defines an interior region which is in fluid communication with an inner channel of the tubular portion 24. In use, the distal end 26 of the tubular portion 24 is connected to one end of the spacer 14, which is connected to a medicament dispenser at the opposite end, and the downstream end 22 of the mask 12 is fitted against the animal's face, covering the animal's mouth and nostrils, so that the device 10 delivers the medicament dispensed from the medicament dispenser, via the spacer 14 and the mask 12, to the animal's mouth and nostrils for inhalation.

FIGS. 10A-13B show the spacer 14, which includes a first elongated cylindrical member 40 extending along a central axis Y between a proximal end 42 and a distal end 44, and a second elongated cylindrical member 46 extending along a central axis Z between a proximal end 48 and a distal end 50. The central axis Y is substantially parallel to the central axis Z. The second cylindrical member 46 is partially cut away along a major portion of its length, and the first cylindrical member 40 is also partially cut away along its length. The major portion of the second cylindrical member 46 and the first cylindrical member 40 are joined together by attaching the cut-away surface of the second cylindrical member 46 to the cut-away surface of the first cylindrical member 40, with a relatively small portion near the proximal end 48 of the second cylindrical member 46 extending beyond the proximal end 42 of the cylindrical member 40 for inserting into the distal end 26 of the mask 12, as shown in FIG. 3 and FIG. 4B. Preferably, the cutting-away surface of the second cylindrical member 46 is a cross section along the central axis Z, as shown in FIG. 10B.

The first cylindrical member 40 has a relatively large diameter in the cross section transverse to the axis Y, and the second cylindrical member 46 has a relatively small diameter in the cross section transverse to the axis Z. The first cylindrical member 40 defines an inner channel extending along the axis Y and passing through the cylindrical member 40, and the second cylindrical member 46 defines an inner channel extending along the axis Z and passing through the second cylindrical, and as shown in FIG. 10B and FIG. 12B, the inner channels of the cylindrical members 40 and 46 are joined and are in communication with each other along their length. As shown in FIG. 12B and FIG. 13B, the first cylindrical member 40 is provided with an inner substantially dome-shaped surface 70 centered about the axis Y at the proximal end 42, facing the incoming air stream directed from the distal end 44 when the device 10 is in use. In use, the inner dome surface 70 deflects the small particles in the medicament in the incoming air stream to allow the small particles to be inhaled through the proximal end 48 of the second cylindrical member 46 and the mask 12, and at the same time, allows the large particles in the medicament to land on the bottom of the inner channel of the first cylindrical member 40. The spacer 14 is preferably integrally constructed and made from a rigid, light-weight, non-porous material, such as a suitable plastic.

FIGS. 14A-18 show various views of the spacer adapter 16, which extends along a central axis W between a proximal end 52 and a distal end 54, and has a shape of two short cylindrical members joined along their length. The spacer adapter 16 has a cross-sectional peripheral profile, which is transverse to the axis W and is similar to the cross-sectional peripheral profile of the spacer 14, with a relatively large diameter first portion 56 and a relatively small diameter second portion 58. The spacer adapter 16 defines a continuous slot 60 along the boundary of the spacer adapter 16. The slot 60 extends a distance along the central axis W from the proximal end 52 to a point near the distal end 54, as shown in FIG. 15B and FIG. 16B. The slot 60 is sized to receive the distal end of the spacer 14, whereby a portion of the slot 60 in the relatively large diameter first portion 56 receives the distal end 44 of the first cylindrical member 40, and the other portion of the slot 60 in the relatively small diameter second portion 58 receives the distal end 50 of the second cylindrical member 46. The spacer adapter 16 is attached to the distal end of the spacer 14 by inserting the distal end of the spacer 14 to the slot 60 of the spacer adapter 16.

The spacer adapter 16 further defines an inlet passageway 64, which extends along the central axis W. The inlet passageway 64 is adapted to receive a mouthpiece of a medicament dispenser, such as an inhaler. In the embodiment shown in FIGS. 15A and 16A, the passageway 64 is provided with a substantially rectangular shape, but the shape of the passageway 64 may vary in different embodiments for use with different medicament dispensers. The spacer adapter 16 is preferably made from a flexible, light-weight, non-porous material, such as a suitable thermoplastic or rubber. The inside structure of the spacer adapter 16 includes peripheral walls of the passageway 64 and webs extending outwardly from the peripheral walls, as shown in FIG. 14B and FIG. 16A. The structure and the material of the spacer adapter 16 provides the spacer adapter 16 with ability to flexibly adapt and accommodate mouthpieces with different sizes or different shapes.

FIGS. 19A-23 show another exemplary embodiment of a spacer adapter 16 for use with a device of the present disclosure. The spacer adapter 16 is similar to the spacer adapter 16 shown in FIGS. 14A through 18, such that similar elements have the same reference characters. FIGS. 24 through 26 show another exemplary embodiment of the delivery device 10, including the spacer adapter 16 of FIGS. 19A-23 attached to the spacer 14.

As shown in FIGS. 19A and 19B, the spacer adapter 16 extends along a central axis W between a proximal end 52 and a distal end 54, and has a shape of two short cylindrical members joined along their length. The spacer adapter 16 defines an inlet passageway 64, which extends along the central axis W from the proximal end 52 to the distal end 54. The inlet passageway 64 is adapted to receive a mouthpiece of a medicament dispenser. In the embodiment shown in FIGS. 19A-23, the inlet passageway 64 is provided with a substantially elliptical shape. In an exemplary form, as shown in FIGS. 21A and 21B, the inlet passageway 64 includes two sections, a first section 65A extending a relatively small distance from the distal end 54 toward the proximal end 52 along the central axis W, and a second section 65B extending from the end of the first section 65A to the proximal end 52. The diameter along a horizontal direction (I-I direction in FIG. 21A) of the second section 65B, as denoted by "D2", is preferably larger than the diameter along the I-I direction of the first section 65A, as denoted by "D1". The inlet passageway 64 receives, secures, and provides a seal around the mouthpiece of the dispensing device when the delivery device 10 is in use.

As shown in FIGS. 19A and 19B, the spacer adapter 16 also defines two hollow regions, a bottom hollow region 82 and a top hollow region 84, respectively positioned below and above the inlet passageway 64 (as shown in the front view in FIG. 19A). Each top and bottom hollow region 82, 84 extend from the distal end 54 toward the proximal end 52 along an axis parallel to the central axis W to an end near the proximal end 52. Two side hollow regions 86 and 88, respectively positioned on the right and on the left of the inlet passageway 64 (as shown in the back view in FIG. 19B), each extend from the proximal end 52 toward the distal end 54 along an axis parallel to the central axis W to an end near the distal end 54.

As shown in the cross-sectional views in FIG. 20B and FIG. 21B, each hollow region extends a major portion of the length of the spacer adapter 16 along W-W direction. In the radial direction, each hollow region extends from an edge near the boundary of the inlet passageway 64 to an edge near the continuous slot 60. The top hollow region 84 preferably has a substantially arcuate shape and the bottom hollow region 82 has a profile similar to the second cylindrical member 46 plus the joint area between the first cylindrical member 40 and the second cylindrical member 46. Two side hollow regions 86 and 88 each have a substantially arcuate shape extending about the central axis W, preferably with a radian of 90 degrees, from a top side edge near the edge of the top hollow region 84 to a bottom side edge near the edge of the bottom hollow region 82. The inside structure of the spacer adapter 16 provides the spacer adapter 16 with flexibility to accommodate mouthpieces with different sizes or different shapes, and also helps to sealingly secure the mouthpiece within the inlet passageway 64.

Figure 16A:
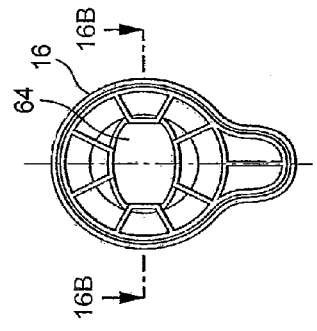
FIG. 16A is a rear elevation view of the spacer adapter of FIGS. 14A and 14B.
Figure 14B:
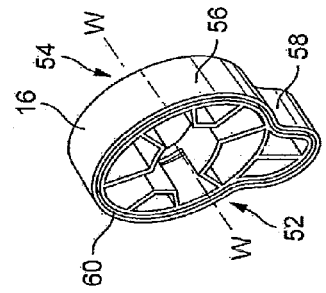
FIGS. 14A and 14B are perspective end views of an exemplary embodiment of an end wall adapter of the device of FIGS. 1A and 1B, that attaches to and closes an end of the spacer of FIGS. 10A and 10B.
Figure 17A:
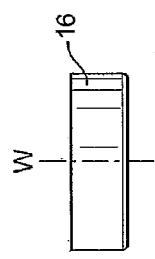
FIG. 17A is a top plan view of the spacer adapter of FIGS. 14A and 14B.
Figure 18:
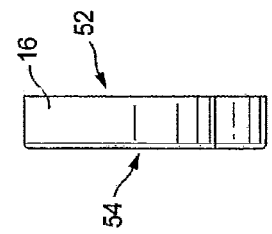
FIG. 18 is a side elevation view of the spacer adapter of FIGS. 14A and 14B.
Figure 14A:
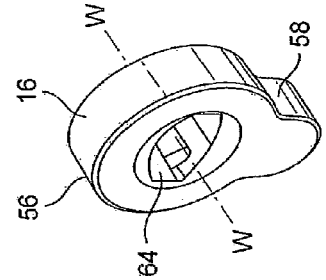
Figure 17B:
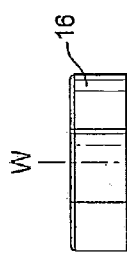
FIG. 17B is a bottom plan view of the spacer adapter of FIGS. 14A and 14B.
Figure 15A:
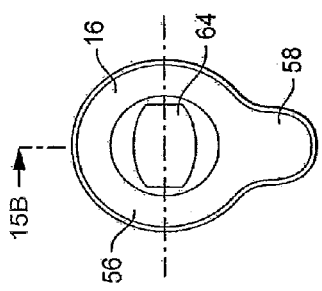
FIG. 15A is a front elevation view of the spacer adapter of FIGS. 14A and 14B.
Figure 15B:
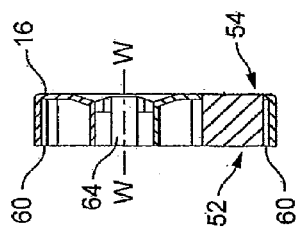
FIG. 15B is a sectional view of the spacer adapter of FIGS. 14A and 14B taken along line 15B-15B in FIG. 15A.
Figure 24:
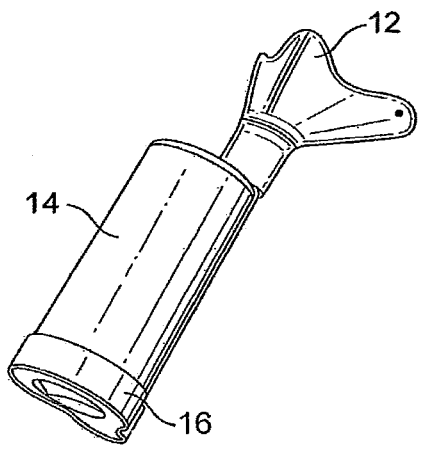
FIG. 24 is a perspective top view of another exemplary embodiment of a delivery device constructed in accordance with the present disclosure and including the spacer adapter of FIGS. 19A and 19B.
Figure 25:
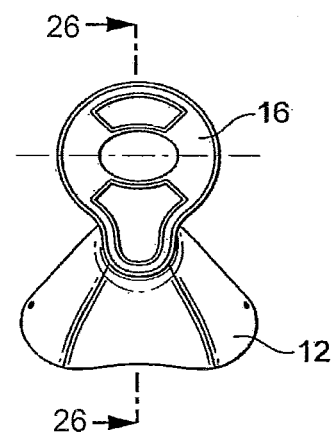
FIG. 25 is end elevation view of the device of FIG. 24.
Figure 26:
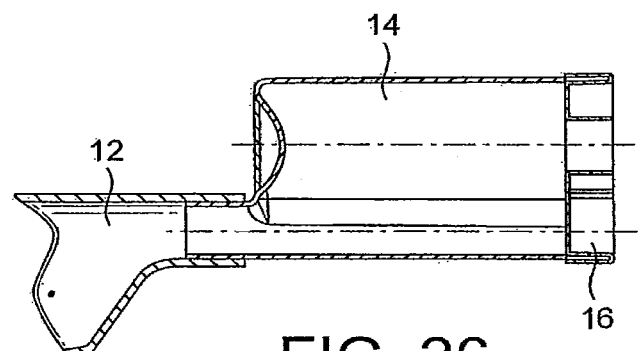
FIG. 26 is a sectional view of the device of FIG. 24 taken along line 26-26 in FIG. 25.

In use, the spacer adapter 16 (applicable to both embodiments illustrated in FIGS. 14A-18 and FIGS. 19-23) is attached to the spacer 14 by sealingly inserting the distal end of the spacer 14 into the slot 60 of the spacer adapter 16, and proximal end 48 of the second cylindrical member 46 of the spacer 14 is inserted into the tubular portion 24 of the mask 12, so that a continuous passageway from the inlet passageway 64 of the spacer adapter 16 to the interior region of the mask 12 is provided. The proximal end 48 of the second cylindrical member 46 is inserted into the tubular portion 24 of the mask 12 in a manner such that a bottom surface 72 of the mask 12 is substantially aligned with a top surface 74 of the first cylindrical member 40, as shown in FIG. 1B and FIG. 4B. In use, a user inserts the mouthpiece of the medicament dispenser into the inlet passageway 64, and presses the mask 12 against the animal's face with the second cylindrical member 46 positioned above the first cylindrical member 40. The animal can breathe in the medicament, which is dispensed into the spacer 14, by its mouth or nostrils through the delivery device 10.

The spacer adapter 16 is preferably shaped to couple to, or receive, an external aerosolizing medicament dispensing device. In various embodiments, the medicament dispensing device may be a metered dose breath-actuated or user (e.g., veterinarian) operated inhaler and may be a dry powder or aerosol dispenser. Preferably, the medicament dispensing device includes an output structure (e.g., a mouthpiece), which directs airborne medicaments to the interior of the passageway 64 of the spacer adapter 16, or directly into the interior of the spacer 14 via the passageway 64 of the spacer adapter 16. The spacer adapter 16 can be manufactured with different sizes and shapes to match the mouthpieces of different medicament dispensers.

FIGS. 27-32 illustrate various views of another exemplary embodiment of a medicament delivery device 10 according to the present disclosure. As shown in the figures, the medicament delivery device 10 further includes a substantially T-shape element 100 extending along the axis Z-Z between the distal end 26 of the mask 12 and the proximal end 48 of the spacer 14, and having two opposite ends respectfully connected to the distal end 26 and the proximal end 48.

One exemplary embodiment of the substantially T-shape element is shown in detail in FIGS. 33A through 39. As best shown in FIGS. 33A and 33B5 the T-shape element 100 includes a first tubular element 102 extending along a central axis between a proximal end 103 and a distal end 104. A second tubular element 106 extends from a middle area of the first tubular element 102, along a central axis perpendicular to the central axis of the first tubular element 102 to a distal end 108. The second tubular element 106 defines an inner channel, which is in fluid communication with an inner channel defined within the first tubular element 102. In an exemplary form, the proximal end 103 of the first tubular element 102 has a diameter adapted for inserting into the distal end 26 of the mask 12, and the distal end 104 has a diameter adapted for receiving the proximal end 48 of the adapter 14.

The T-shape element 100 further includes an inhalation valve 110 disposed inside the inner channel of the first tubular element 102 in a portion between the middle area from which the second tubular element 106 extends and the distal end 104, and an exhalation valve 112 disposed inside the second tubular element 106. Both the inhalation valve 110 and the exhalation valve 112 are preferably one-way valves, such that the inhalation valve 110 allows air to pass through from the distal end 104 to the proximal end 103 of the first tubular element 102, and prevents air from flowing backwards, and the exhalation valve 112 allows air to exit from the inside of the T-shape element 100 to the outside through the distal end 108 of the second tubular element 106, and prevents air from flowing backwards.

As shown in FIG. 33A through FIG. 42, each of the valves 110, 112 includes a plate 120, made from a rigid material. The plate 120 defines one or a plurality of openings 122 for air to pass through. A flexible cover 124 is attached to the plate 120 by a pin 126 (sometimes referred to as an umbrella valve member), which is inserted into and secured in a hole 128 defined in the plate 120. The cover 124 is thin and flexible such that, when air flows in a direction from the openings 122 to the cover 124, the air flips up the cover 124 and passes through the valve, and when air flows in an opposite direction, the air presses the cover 124 against the plate 120, and the plate 120 prevents the cover 124 from moving, and thereby preventing air from passing through the valve.

In use, when a mammal inhales, the inhalation valve 110 is opened by the air pressure, allowing air carrying medicament to pass through from the spacer 14 to the mask 12, and the exhalation valve 112 is closed by the air pressure, preventing air from entering into the delivery device 10. When a mammal exhales, the exhalation valve 112 is opened by the air pressure, allowing air to exit the delivery device 10 through the second tubular element 106, and at the same time, the inhalation valve 110 is closed by the air pressure, preventing the exhaled air from entering into the spacer 14. Other one-way valves having the same or similar function but with various designs could be used with the medicament delivery device 10. The present disclosure should not be limited to the exemplary valve design depicted above and in the figures.

Figure 58:
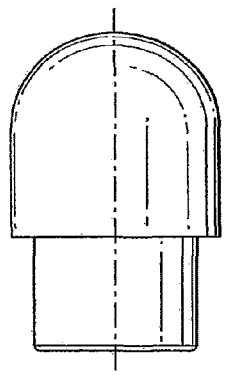
FIG. 58 is a top plan view of the elbow of FIG. 55.
Figure 62:
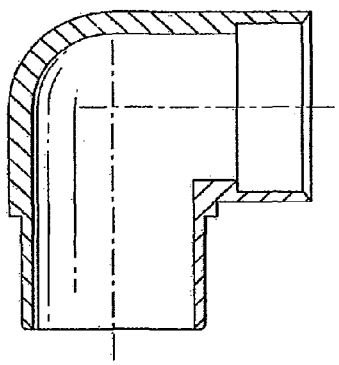
FIG. 62 is a sectional view of the elbow of FIG. 55 taken along the line 62-62 in FIG. 60.
Figure 59:
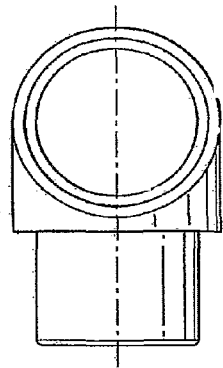
FIG. 59 is a bottom plate view of the elbow of FIG. 55.
Figure 56:
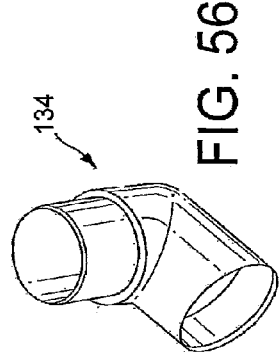
FIGS. 55 and 56 are perspective end views of an elbow of the delivery devices of FIGS. 43 through 54.
Figure 60:
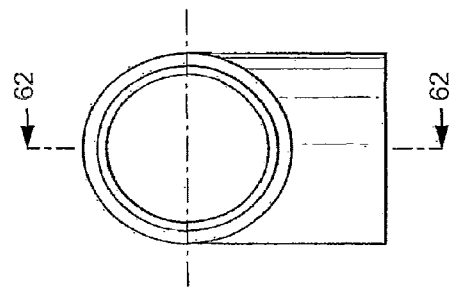
FIG. 60 is an end elevational view of the elbow of FIG. 55.
Figure 57:
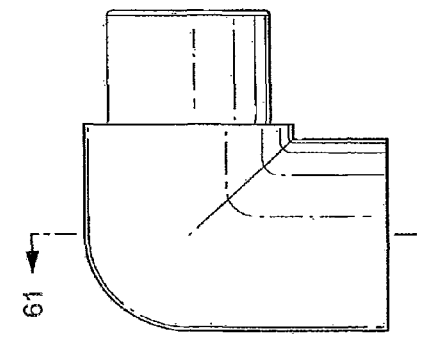
FIG. 57 is a side elevational view of the elbow of FIG. 55.
Figure 55:
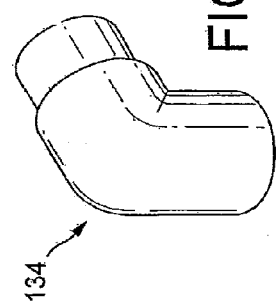
Figure 61:
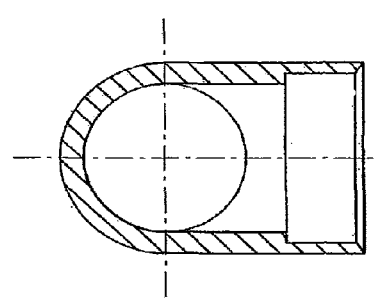
FIG. 61 is a sectional view of the elbow of FIG. 55 taken along line 61-61 in FIG. 57.

FIGS. 43 through 48 illustrate another exemplary embodiment of the medicament delivery device according to the present disclosure. The medicament delivery device 200 includes a mask 12 and a nebulizer 130 connected to the mask 12 by an elongated hose 132. The mask 12 is similar to the mask described in the previous embodiments. The nebulizer 130 contains and/or converts medication to a fine spray adapted for inhalation by a mammal. The hose 132 preferably is flexible and has a bellow shape, and the length of the hose 132 is adjustable. A proximal end of the hose 132 is connected to the distal end 26 of the mask, and the other end (distal end) is connected to the nebulizer 130 by an elbow 134, which is shown in detail in FIGS. 55-62.

Figure 33B:
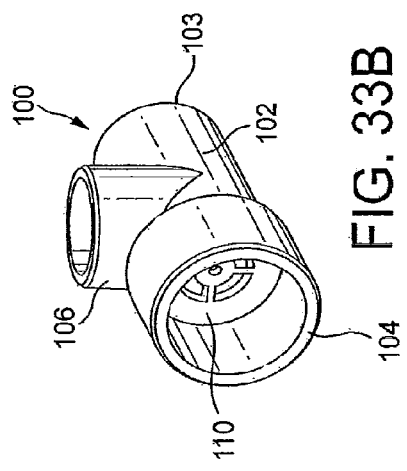
FIGS. 33A and 33B are perspective end views of the T-shape element of the delivery device of FIGS. 27 and 28.
Figure 34:
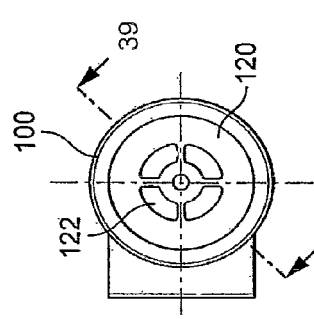
FIG. 34 is a side elevation view of the T-shape element of FIGS. 33A and 33B.
Figure 36:
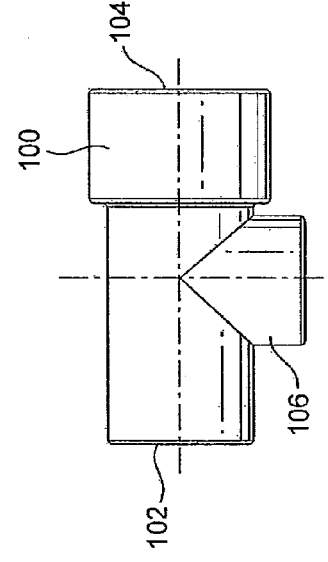
FIG. 36 is an end elevation view of the T-shape element of FIGS. 33A and 33B.
Figure 35:
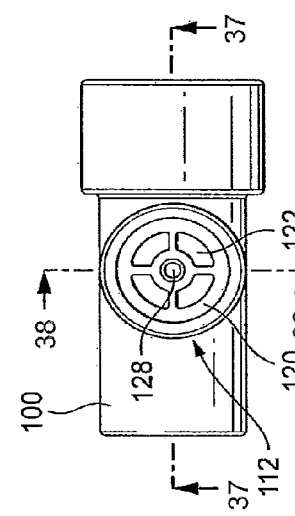
FIG. 35 is a top plan view of the T-shape element of FIGS. 33A and 33B.
Figure 39:
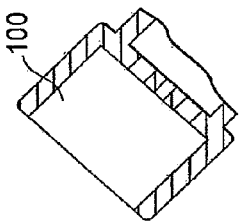
FIG. 39 is a sectional view of the T-shape element of FIGS. 33A and 33B taken along line 39-39 in FIG. 36.
Figure 33A:
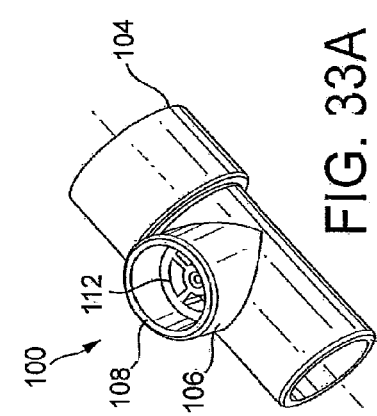
Figure 38:
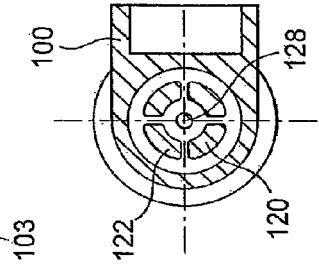
FIG. 38 is a sectional view of the T-shape element of FIGS. 33A and 33B taken along line 38-38 in FIG. 35.
Figure 37:
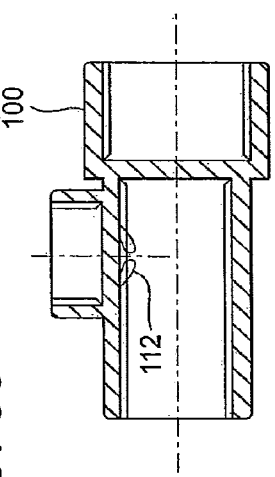
FIG. 37 is a sectional view of the T-shape element of FIGS. 33A and 33B taken along line 37-37 in FIG. 35.
Figure 42:
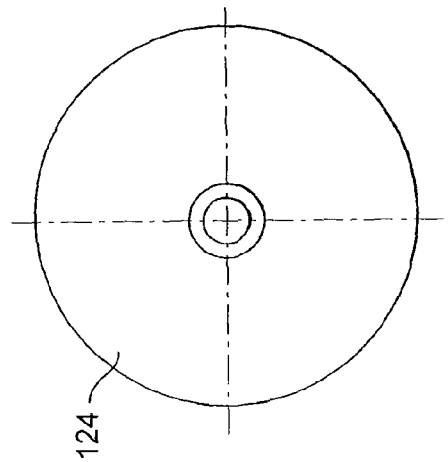
FIG. 42 is an opposite end plan view of the valve member of FIG. 40.
Figure 40:
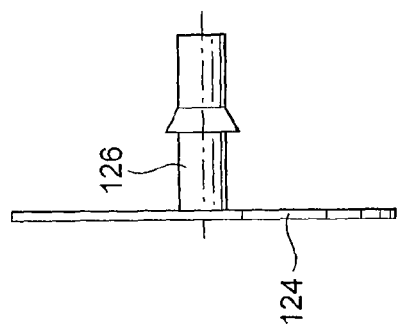
FIG. 40 is a side elevation view of a valve member for use with the T-shape element of FIGS. 33A and 33B.
Figure 41:
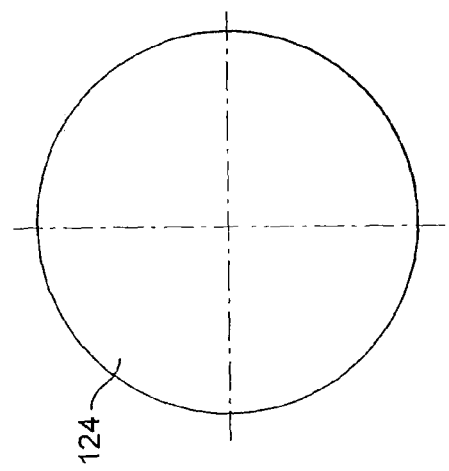
FIG. 41 is an end plan view of the valve member of FIG. 40.

FIGS. 49-54 illustrate another exemplary embodiment of the medicament delivery device 200, which is similar to the device illustrated in FIGS. 43-48, except that the proximal end of the hose 132 is connected to the distal end 26 of the mask 12 by a T-shape element 100, which has two one-way valves 110 and 112, similar to the T-shape element 100 described in previous embodiments and depicted in FIGS. 27-42.

FIGS. 55-62 illustrate various views of the elbow 134. As shown in the figures, the elbow 134 preferably has two sections joined at an angle of about 90 degrees. One section is connected to the distal end of the hose 132 and the other section is connected to the nebulizer 130.

The delivery device 10 or 200 may be used for any drug formulation which may be advantageously administered to the lung or nasal passages in an animal, to cure or alleviate any illness or its symptoms. Many medicaments, bioactive active substances and pharmaceutical compositions may be included in the dosage forms of the present disclosure. Non-limiting examples of classes of drugs contemplated for use include ace-inhibitors, acne drugs, alkaloids, amino acid preparations, anabolic preparations, analgesics, anesthetics, antacids, antianginal drugs, anti-anxiety agents, anti-arrhythmias, anti-asthmatics, antibiotics, anti-cholesterolemics, anti-coagulants, anti-convulsants, anti-depressants, anti-diabetic agents, anti-diarrhea preparations, antidotes, anti-emetics, anti-histamines, anti-hypertensive drugs, anti-inflammatory agents, anti-lipid agents, anti-manics, anti-nauseants, anti-nauseants, anti-neoplastics, anti-obesity drugs, anti-parkinsonism agents, anti-psychotics, anti-pyretics, anti-rheumatic agents, anti-spasmodics, anti-stroke agents, anti-thrombotic drugs, anti-thyroid preparations, anti-tumor drugs, anti-tussives, anti-ulcer agents, anti-uricemic drugs, anti-viral drugs, appetite stimulants or suppressants, biological response modifiers, blood modifiers, bone metabolism regulators, cardiovascular agents, central nervous system stimulates, cerebral dilators, cholinesterase inhibitors, contraceptives, coronary dilators, cough suppressants, decongestants, dietary supplements, diuretics, DNA and genetic modifying drugs, dopamine receptor agonists, endometriosis management agents, enzymes, erectile dysfunction therapies, erythropoietic drugs, expectorants, fertility agents, gastrointestinal agents, homeopathic remedies, hormones, hyper- and hypo-glycemic agents, hypercalcemia and hypocalcemia management agents, hypnotics, immunomodulators, immunosuppressives, ion exchange resins, laxatives, migraine preparations, motion sickness treatments, mucolytics, muscle relaxants, neuromuscular drugs, obesity management agents, osteoporosis preparations, oxytocics, parasympatholytics, parasympathomimetics, peripheral vasodilators, prostaglandins, psychotherapeutic agents, psycho-tropics, stimulants, respiratory agents, sedatives, smoking cessation aids, sympatholytics, systemic and non-systemic anti-infective agents, terine relaxants, thyroid and anti-thyroid preparations, tranquilizers, tremor preparations, urinary tract agents, vasoconstrictors, vasodilators, and combinations thereof.

The present disclosure may be embodied in other specific forms and embodiments without departing from the spirit or essential characteristics thereof. The exemplary embodiments shown in the present specification are, therefore, to be considered in all respects illustrative and not restrictive, of the scope of the present disclosure, and all changes which come within the meaning and range of equivalency of the exemplary embodiments are therefore intended to be embraced within the present disclosure.

What is claimed is:

1. A spacer for connecting an inhaler device to a mask, the spacer comprising:
   a) an elongated cylindrical first member extending along a first central axis between a distal end of the first member adapted to receive an inhaler device and a proximal end of the first member having a particle reflecting surface, and wherein the first member has a first inner channel having a length extending along the first central axis;
   b) an elongated cylindrical second member extending along a second central axis between a closed distal end of the second member and a proximal end of the second member adapted to connect to a mask, wherein the second member defines a second inner channel extending along the second central axis of the second member and wherein the first member and the second member are connected such that the first and second inner channels of the first and second members are joined lengthwise at a longitudinal junction,
   wherein the first inner channel is open to the second inner channel along an entirety of the length of the first inner channel at the longitudinal junction,
   wherein the particle reflecting surface of the proximal end of the first member is substantially dome-shaped and extends towards the distal end of the first member.

2. A spacer according to claim 1, wherein the second central axis of the second member is substantially parallel to the first central axis of the first member.

3. A spacer according to claim 1, wherein the first member has a cross-sectional diameter that is larger than a cross-sectional diameter of the second member.

4. A spacer according to claim 1, wherein the distal end of the second member and the distal end of the first member lie within a transverse plane extending generally orthogonal to the first and second central axes.

5. A spacer according to claim 1, wherein the proximal end of the second member extends beyond the proximal end of the first member.

6. A spacer according to claim 1, wherein the second member and the first member are integrally formed and made from a rigid, light-weight, non-porous material.

7. A spacer according to claim 1, further comprising an adapter closing the distal end of the first member and defining an inlet passageway for receiving a mouthpiece of an inhaler, wherein the adapter is made of a flexible resilient material such that the inlet passageway can accommodate various mouthpieces having different sizes and shapes.

8. A medicament delivery device comprising:
a spacer for connecting an inhaler device to a mask, the spacer including
a) an elongated cylindrical first member extending along a first central axis between a distal end of the first member adapted to receive an inhaler device and a proximal end of the first member having a particle reflecting surface, and wherein the first member has a first inner channel having a length extending along the first central axis, and
b) an elongated cylindrical second member extending along a second central axis between a closed distal end of the second member and a proximal end of the second member adapted to connect to a mask, wherein the second member defines a second inner channel extending along the second central axis of the second member and wherein the first member and the second member are connected such that the first and second inner channels of the first and second members are joined lengthwise at a longitudinal junction, wherein the first inner channel is open to the second inner channel along an entirety of the length of the first inner channel at the longitudinal junction, wherein the particle reflecting surface of the proximal end of the first member is substantially dome-shaped and extends towards the distal end of the first member; and
a mask connected to the proximal end of the second member.

9. A medicament delivery device according to claim 8, further comprising a one-way inhalation valve secured to the proximal end of the second member.

10. A medicament delivery device comprising:
a spacer for connecting an inhaler device to a mask, the spacer including
a) an elongated cylindrical first member extending along a first central axis between a distal end of the first member adapted to receive an inhaler device and a proximal end of the first member having a particle reflecting surface, and wherein the first member has a first inner channel having a length extending along the first central axis, and
b) an elongated cylindrical second member extending along a second central axis between a closed distal end of the second member and a proximal end of the second member adapted to connect to a mask, wherein the second member defines a second inner channel extending along the second central axis of the second member and wherein the first member and the second member are connected such that the first and second inner channels of the first and second members are joined lengthwise at a longitudinal junction, wherein the first inner channel is open to the second inner channel along an entirety of the length of the first inner channel at the longitudinal junction, wherein the particle reflecting surface of the proximal end of the first member is substantially dome-shaped and extends towards the distal end of the first member; and
a T-shape element including, a first tubular element extending along a third central axis between a distal end of the first tubular element connected to the proximal end of the second member of the spacer and a proximal end of the first tubular element for connection to a mask, and a second tubular element extending from the first tubular element along a fourth central axis of the second tubular element that is perpendicular to the third central axis of the first tubular element.

11. A medicament delivery device according to claim 10, further comprising a mask connected to the proximal end of the first tubular element of the T-shape element.

12. A medicament delivery device according to claim 10, wherein the T-shape element further includes a one-way inhalation valve positioned in the distal end of the first tubular element.

13. A medicament delivery device according to claim 10, wherein the T-shape element further includes a one-way exhalation valve disposed inside the second tubular element.

14. A medicament delivery device according to claim 8, further comprising an inhaler connected to the distal end of the first member.

15. A medicament delivery device according to claim 14, wherein the inhaler includes a medicament container.

16. A medicament delivery device according to claim 15, wherein the medicament container contains a medicament selected from a group consisting of acne-inhibitors, acne drugs, alkaloids, amino acid preparations, anabolic preparations, analgesics, anesthetics, antacids, antianginal drugs, anti-anxiety agents, anti-arrhythmias, anti-asthmatics, antibiotics, anti-cholesterolemics, anti-coagulants, anti-convulsants, anti-depressants, anti-diabetic agents, anti-diarrhea preparations, antidotes, anti-emetics, anti-histamines, anti-hypertensive drugs, anti-inflammatory agents, anti-lipid agents, anti-manics, anti-nauseants, anti-nauseants, anti-neoplasties, anti-obesity drugs, anti-parkinsonism agents, anti-psychotics, anti-pyretics, anti-rheumatic agents, anti-spasmodics, anti-stroke agents, anti-thrombotic drugs, anti-thyroid preparations, anti-tumor drugs, anti-tussives, anti-ulcer agents, anti-uricemic drugs, anti-viral drugs, appetite stimulants or suppressants, biological response modifiers, blood modifiers, bone metabolism regulators, cardiovascular agents, central nervous system stimulates, cerebral dilators, cholinesterase inhibitors, contraceptives, coronary dilators, cough suppressants, decongestants, dietary supplements, diuretics, DNA and genetic modifying drugs, dopamine receptor agonists, endometriosis management agents, enzymes, erectile dysfunction therapies, erythropoietic drugs, expectorants, fertility agents, gastrointestinal agents, homeopathic remedies, hormones, hyper- and hypo-glycemic agents, hypercalcemia and hypocalcemia management agents, hypnotics, immunomodulators, immunosuppressives, ion exchange resins, laxatives, migraine preparations, motion sickness treatments, mucolytics, muscle relaxants, neuromuscular drugs, obesity management agents, osteoporosis preparations, oxytocics, parasympatholytics, parasympathomimetics, peripheral vasodilators, prostaglandins, psychotherapeutic agents, psycho-tropics, stimulants, respiratory agents, sedatives, smoking cessation aids, sympatholytics, systemic and non-systemic anti-infective agents, terine relaxants, thyroid and anti-thyroid preparations, tranquilizers, tremor preparations, urinary tract agents, vasoconstrictors, vasodilators, and combinations thereof.

17. A medicament delivery device according to claim 8, wherein the mask includes a base portion having an upstream end and an open downstream end that is larger than the upstream end and adapted for fitting over a face, and a tubular portion extending from the upstream end of the base portion to a distal end connected to the proximal end of the second member of the spacer.

18. A medicament delivery device according to claim 17, wherein the mask is made from a flexible, lightweight, non-porous material.

19. A medicament delivery device according to claim 17, wherein the downstream end of the mask includes a bottom edge section, and two side edge sections extending from ends of the bottom edge section and joined at the top of the downstream end, wherein the bottom edge section is slightly curved toward the upstream end in a substantially V-shape, and the side edge sections are slightly curved, from the bottom edge section, first towards the upstream end and then, away from the upstream end to form a substantially S-shape periphery.

* * * * *